(12) United States Patent
Lin et al.

(10) Patent No.: US 6,528,256 B1
(45) Date of Patent: Mar. 4, 2003

(54) METHODS FOR IDENTIFICATION AND ISOLATION OF SPECIFIC NUCLEOTIDE SEQUENCES IN CDNA AND GENOMIC DNA

(75) Inventors: Jhy-Jhu Lin, Potomac, MD (US); Jonathan Kuo, Germantown, MD (US); Wu-Bo Li, Gaithersburg, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/603,613

(22) Filed: Jun. 26, 2000

Related U.S. Application Data (63) Continuation of application No. 08/920,889, filed on Aug. 29, 1997, now abandoned.
(60) Provisional application No. 60/028,519, filed on Oct. 18, 1996, and provisional application No. 60/024,864, filed on Aug. 30, 1996.

(51) Int. Cl.[7] .................. C12Q 1/68; C07H 21/102; C07H 21/04

(52) U.S. Cl. .................. 435/6; 536/23.1; 536/24.3

(58) Field of Search .................. 455/6; 536/26.6

(56) References Cited

U.S. PATENT DOCUMENTS

| | | | |
|---|---|---|---|
| 5,075,217 A | 12/1991 | Weber | 435/6 |
| 5,306,616 A | 4/1994 | Lupski et al. | 435/6 |
| 5,364,759 A | 11/1994 | Caskey et al. | 435/6 |
| 5,369,004 A | 11/1994 | Polymeropoulos et al. | 435/6 |
| 5,378,602 A | 1/1995 | Polymeropoulos et al. | 435/6 |
| 5,409,818 A | 4/1995 | Davey et al. | 435/91.21 |
| 5,413,908 A | 5/1995 | Jeffreys | 435/6 |
| 5,420,029 A | 5/1995 | Gelfand et al. | 435/194 |
| 5,436,142 A | 7/1995 | Wigler et al. | 435/91.2 |
| 5,436,149 A | 7/1995 | Barnes | 435/194 |
| 5,455,166 A | 10/1995 | Walker | 435/91.2 |
| 5,459,039 A | 10/1995 | Modrich et al. | 435/6 |
| 5,466,591 A | 11/1995 | Abramson et al. | 435/194 |
| 5,468,610 A | 11/1995 | Polymeropoulos et al. | 435/6 |
| 5,468,613 A | 11/1995 | Erlich et al. | 435/6 |
| 5,489,523 A | 2/1996 | Mathur | 435/194 |
| 5,541,099 A | 7/1996 | Chatterjee | 435/194 |
| 5,556,955 A | 9/1996 | Vergnaud | 536/24.31 |
| 5,565,340 A | 10/1996 | Chenchik et al. | 435/91.2 |
| 5,599,672 A | 2/1997 | Liang et al. | 435/6 |
| 5,618,711 A | 4/1997 | Gelfand et al. | 435/194 |
| 5,624,833 A | 4/1997 | Gelfand et al. | 435/194 |
| 5,674,993 A | 10/1997 | Kawasaki et al. | 536/23.6 |
| 5,691,136 A | 11/1997 | Lupski et al. | 435/6 |
| 5,700,644 A | * 12/1997 | Gould et al. | |
| 5,766,847 A | 6/1998 | Jäckle et al. | 435/6 |
| 5,885,813 A | 3/1999 | Davis et al. | 435/183 |
| 5,912,155 A | 6/1999 | Chatterjee et al. | 435/194 |
| 5,939,301 A | 8/1999 | Hughes, Jr. et al. | 435/194 |
| 5,948,614 A | 9/1999 | Chatterjee | 435/6 |
| 6,001,645 A | 12/1999 | Slater et al. | 435/320.1 |
| 6,015,668 A | 1/2000 | Hughes et al. | 435/6 |
| 6,045,994 A | 4/2000 | Zabeau et al. | 435/6 |
| 6,077,664 A | 6/2000 | Slater et al. | 435/6 |

FOREIGN PATENT DOCUMENTS

| | | |
|---|---|---|
| DE | 38 34 636 A1 | 4/1990 |
| EP | 0 329 822 A2 | 8/1989 |
| EP | 0 534 858 A1 | 3/1993 |
| EP | 0 684 315 A1 | 11/1995 |
| EP | 0 892 058 A2 | 1/1999 |
| WO | WO 93/06239 | 4/1993 |
| WO | WO 95/13369 | 5/1995 |
| WO | WO 96/10640 | 4/1996 |
| WO | WO 96/27680 | 9/1996 |
| WO | WO 96/41014 | 12/1996 |
| WO | WO 97/09451 | 3/1997 |
| WO | WO 97/37042 | 10/1997 |
| WO | WO 98/23733 | 6/1998 |

OTHER PUBLICATIONS

Wang et al., A Gene Expression Screen PNAS 88: 11505–11509 (1991).*
Frohman et al., 85: 8998–9002 (1988).*
Liang et al., International J. of Oncology 7: 611–615 (1995).*
Adams, M.D., et al., "Sequence identification of 2,375 human brain genes," *Nature* 355:632–634, Macmillan Publishers Ltd. (1992).
Bachem, C.W.B., et al., "Visualization of differential gene expression using a novel method of RNA fingerprinting based on AFLP: Analysis of gene expression during potato tuber development," *Plant J.* 9:745–753, Oxford Bios Scientific Publishers And Blackwell Scientific Publications In Association With The Society For Experimental Biology (May 1996).
Botstein, D., et al., "Construction of a Genetic Linkage Map in Man Using Restriction Fragment Length Polymorphisms," *Am. J. Human Genetics* 32:314–331, University of Chicago Press (1980).
Brown, W.R.A., et al., "Structure and Polymorphism of Human Telomere–Associated DNA," *Cell* 63:119–132, Cell Press (1990).

(List continued on next page.)

Primary Examiner—Ethan C. Whisenant
(74) Attorney, Agent, or Firm—Sterne, Kessler, Goldstein & Fox P.L.L.C.

(57) ABSTRACT

The present invention is directed to a method for the identification and isolation of specific genetic sequences from cDNA libraries or samples of genomic DNA derived from the cells, tissues or organs of an organism, particularly a mammal, and most particularly a human (including a human embryo or fetus). In particular, the invention is related to a method whereby a tissue-specific cDNA or a genetic marker, not found in cDNA libraries or genomic DNA samples derived from other tissues from the same or a different organism, may be identified and isolated using an Amplification Fragment Length Polymorphism (AFLP)-based technique. This method has applications in the identification and isolation of cDNA sequences and genomic genetic markers which may be used in a variety of medical, forensic, industrial and plant breeding procedures.

42 Claims, 5 Drawing Sheets-

OTHER PUBLICATIONS

Caetano–Anollés, G., et al., "DNA Amplification Fingerprinting Using Very Short Arbitrary Oligonucleotide Primers," *Bio/Technol. 9:*553–557, Nature Publishing Co. (1991).

Cochran, B.H., et al., "Expression of the c–fos Gene and of an fos–Related Gene Is Stimulated by Platelet–Derived Growth Factor," *Science 226:*1080–1082, American Association for the Advancement of Science (1984).

Erlich, H.A., et al., "Recent Advances in the Polymerase Chain Reaction," *Science 252:*1643–1650, American Association for the Advancement of Science (1991).

Gubler, U., and Hoffman, B.J., "A simple and very efficient method for generating cDNA libraries," *Gene 25:*263–269, Elsevier/North–Holland (1983).

Habu, Y., et al., "Amplified Restriction Fragment Length Polymorphism–Based mRNA Fingerprinting Using a Single Restriction Enzyme That Recognizes a 4–bp Sequence," *Biochem. Biophys. Res. Comm. 234:*516–521, Academic Press, Inc. (May 19, 1997).

Heath, D.D., et al., "PCR primed with VNTR core sequences yields species specific patterns and hypervariable probes," *Nucl. Acids. Res. 21:*5782–5785, Oxford University Press (1993).

Hedrick, S.M., et al., "Isolation of cDNA clones encoding T cell–specific membrane–associated proteins," *Nature 308:*149–153, Macmillan Publishers Ltd. (1984).

Hite, J.M., et al., "Factors affecting fidelity of DNA synthesis during PCR amplification of $d(C-A)_n-d(G-T)_n$ microsatellite repeats," *Nucl. Acids Res. 24:*2429–2434, Oxford University Press (Jun. 15, 1996).

Holmstrøm, K., et al., "A Highly Sensitive and Fast Non-radioactive Method for Detection of Polymerase Chain Reaction Products," *Anal. Biochem. 209:*278–283, Academic Press, Inc. (1993).

Ivanova, N.B., and Belyavsky, A.V., "Identification of differentially expressed genes by restriction endonuclease–based gene expression fingerprinting," *Nucl. Acids Res. 23:*2954–2958, Oxford University Press (Aug. 1995).

Klausner, A., and Wilson, T., "Gene Detection Technology Opens Doors for Many Industries," *Bio/Technol.*, p. 471–478, Nature Publishing Co. (1983).

Lau, L.F., and Nathans, D., "Identification of a set of genes expressed during the G0/G1 transition of cultured mouse cells," *EMBO J. 4:*3145–3151, IRL Press Limited (1985).

Lee, C.C., et al., "Generation of cDNA Probes Directed by Amino Acid Sequence: Cloning of Urate Oxidase," *Science 239:*1288–1291, American Association for the Advancement of Science (1988).

Lin, J.–J., et al., "DH12S: A New Electrocompetent *E. coli* Strain for the Production of Highly Purified Single–Stranded DNA Using Phagemid Vectors," *FOCUS 14(3):*98–101, Life Technologies, Inc. (1992).

Lin, J.–J., and Kuo, J., "AFLP™: A Novel PCR–Based Assay for Plant and Bacterial DNA Fingerprinting," *FOCUS 17(2):*66–70, Life Technologies, Inc. (Jun. 1995).

Lin, J.–J., et al., "Identification of Molecular Markers in Soybean Comparing RFLP, RAPD and AFLP DNA Mapping Techniques," *Plant Mol. Biol. Reporter 14:*156–169, Mary Ann Liebert, Inc. (Jun. 1996).

Lin, J.–J., et al., "Effect of Different Primer Combinations on the Resolution of AFLP™ in Plants with Small Genomes," *FOCUS 18(3):*68–69, Life Technologies, Inc. (Nov. 1996).

Lin, J.–J., et al., "Chemiluminescent Detection of AFLP™ Fingerprints," *FOCUS 19(2):*36–38, Life Technologies, Inc. (Jul. 1997).

Maniatis, T., et al., "The Isolation of Structural Genes from Libraries of Eucaryotic DNA," *Cell 15:*687–701, MIT Press (1978).

Money, T., et al., "AFLP–based mRNA fingerprinting," *Nucl. Acids Res. 24:*2616–2617, Oxford University Press (Jul. 1996).

Okayama, H., and Berg, P., "High–Efficiency Cloning of Full–length cDNA," *Mol. Cell. Biol. 2:*161–170, American Society for Microbiology (1982).

Richardson, T., et al., "Hybridization of microsatellites to RAPD: a new source of polymorphic markers," *Nucl. Acids Res. 23:*3798–3799, Oxford University Press (1995).

Rigas, B., et al., "Rapid plasmid library screening using RecA–coated biotinylated probes," *Proc. Natl. Acad. Sci. USA 83:*9591–9595, National Academy of Sciences of the USA (1986).

Sambrook, J., et al., "Transfer of DNA from Agarose Gels to Nylon Membranes," in *Molecular Cloning, a Laboratory Manual,* $2^{nd}$ Ed., Cold Spring Harbor Laboratory Press, pp. 9.42–9.43; 9.58 (1989).

Suzuki, M., et al., "Random Mutagenesis of *Thermus aquaticus* DNA polymerase I: Concordance of immutable sites in vivo with the crystal structure," *Proc. Natl. Acad. Sci. USA 93:*9670–9675, National Academy of Sciences of the USA (Sep. 1996).

Suzuki, M., et al., "Low Fidelity Mutants in the O–Helix of *Thermus aquaticus* DNA polymerase I," *J. Biol. Chem. 272:*11228–11235, American Society for Biochemistry and Molecular Biology, Inc. (Apr. 25, 1997).

Tanksley, S.D., et al., "RFLP Mapping in Plant Breeding: New Tools for an Old Science," *Bio/Technol. 7:*257–264, Nature Publishing Co. (1989).

Tsurai, H., et al., "A Rapid and Efficient Cloning Method with a Solid–Phase DNA Probe: application for cloning the 5' flanking region of the gene encoding human fibronectin," *Gene 88:*233–239, Elsevier/North–Holland (1990).

Vos, et al., "AFLP: a new technique for DNA fingerprinting," *Nucl. Acids Res. 23:*4407–4414 (1995).

Watson, J.D., et al., "DNA–Based Diagnosis of Genetic Diseases," in *Recombinant DNA,* $2^{nd}$ Ed., Scientific American Books, pp. 539–566 (1992).

Welsh, J., and McClelland, M., "Fingerprinting genomes using PCR with arbitrary primers," *Nucl. Acids. Res. 18:*7213–7218, Oxford University Press (1990).

White, R., and Laloul, J.–M., "Chromosome Mapping with DNA Markers," *Scientific Am. 258:*40–48, Scientific American (1988).

Wilks, A.F., "Two putative protein–tyrosine kinases identified by application of the polymerase chain reaction," *Proc. Natl. Acad. Sci. USA 86:*1603–1607, National Academy of Sciences of the USA (1989).

Williams, J.G.K., et al., "DNA polymorphisms amplified by arbitrary primers are useful as genetic markers," *Nucl. Acids Res. 18:*6531–6535, Oxford University Press (1990).

Yunis, I., et al., "HLA–DR generic typing by AFLP," *Tissue Antigens 38:*78–88, Copenhagen International Booksellers Publishers (1991).

English language abstract of DE 38 34 636 A (Document No. AM1). [retrieved from Derwent World Patents Index, Dialog file 351, Accession No. 1990–156806/199021].

* cited by examiner

METHODS FOR IDENTIFICATION AND ISOLATION OF SPECIFIC NUCLEOTIDE SEQUENCES IN CDNA AND GENOMIC DNA

CROSS REFERENCE TO RELATED APPLICATIONS

This application is a continuation of U.S. application Ser. No. 08/920,889, filed Aug. 29, 1997 (now abandoned), which claims priority to U.S. application Ser. No. 60/024,864, filed Aug. 30, 1996, and to U.S. application Ser. No. 60/028,519, filed Oct. 18, 1996, the disclosures of which are incorporated herein in their entireties.

BACKGROUND OF THE INVENTION

1. Field of the Invention

This invention is in the field of molecular and cellular biology. In general, the invention is related to a method for the identification and isolation of specific genetic sequences or genetic markers from the genomic DNA or cDNA of an organism. In particular, the invention is related to a method whereby a DNA fragment from a first sample of genomic DNA or cDNA, not found in a second sample of genomic DNA or cDNA, may be identified and isolated via a series of digestion, amplification, purification and sequencing steps. This invention has utility in the identification and isolation of genomic DNA or cDNA sequences that may serve as genetic markers for use in a variety of medical, forensic, industrial and plant breeding procedures.

2. Related Art

Genomic DNA

In examining the structure and physiology of an organism, tissue or cell, it is often desirable to determine its genetic content. The genetic framework (i.e., the genome) of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene ultimately encodes. In order to produce a protein, a complementary copy of one strand of the DNA double helix (the "sense" strand) is produced by polymerase enzymes, resulting in a specific sequence of messenger ribonucleic acid (mRNA). This mRNA is then translated by the protein synthesis machinery of the cell, resulting in the production of the particular protein encoded by the gene. There are additional sequences in the genome that do not encode a protein (i.e., "noncoding" regions) which may serve a structural, regulatory, or unknown function. Thus, the genome of an organism or cell is the complete collection of protein-encoding genes together with intervening noncoding DNA sequences. Importantly, each somatic cell of a multicellular organism contains the full complement of genomic DNA of the organism, except in cases of focal infections or cancers, where one or more xenogeneic DNA sequences may be inserted into the genomic DNA of specific cells and not into other, non-infected, cells in the organism. As noted below, however, the expression of the genes making up the genomic DNA may vary between individual cells.

cDNA and cDNA Libraries

Within a given cell tissue or organism, there exist myriad mRNA species, each encoding a separate and specific protein. This fact provides a powerful tool to investigators interested in studying genetic expression in a tissue or cell—mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or hydroxyapatite, to which oligomers of deoxythymidine (dT) have been complexed. Since the 3' termini on all eukaryotic mRNA molecules contain a string of deoxyadenosine (dA) bases, and since dA binds to dT, the mRNA molecules can be rapidly purified from other molecules and substances in the tissue or cell extract. From these purified mRNA molecules, cDNA copies may be made using the enzyme reverse transcriptase, which results in the production of single-stranded cDNA molecules. The single-stranded cDNAs may then be converted into a complete double-stranded DNA copy of the original mRNA (and thus of the original double-stranded DNA sequence, encoding this mRNA, contained in the genome of the organism) by the action of a DNA polyinerase. The protein-specific double-stranded cDNAs can then be inserted into a plasmid, which is then introduced into a host bacterial cell. The bacterial cells are then grown in culture media, resulting in a population of bacterial cells containing (or in many cases, expressing) the gene of interest.

This entire process, from isolation of mRNA to insertion of the cDNA into a plasmid to growth of bacterial populations containing the isolated gene, is termed "cDNA cloning." If cDNAs are prepared from a number of different mRNAs, the resulting set of cDNAs is called a "cDNA library," representing the different functional (i.e., expressed) genes present in the source cell, tissue or organism. Genotypic analysis of these cDNA libraries can yield much information on the structure and function of the organisms from which they were derived.

DNA Fingerprinting

To determine the genotype of an organism, tissue or cell, a variety of molecular biological techniques are employed. These techniques allow researchers, clinicians, forensic scientists and others to probe for the presence of specific genes in the samples which are being studied. The results of such analyses may be useful to researchers in examining the phylogenetic relationship between two organisms, to clinicians in determining whether an individual is infected with a particular disease or is a carrier of a disease-related gene, and to forensic scientists in analyzing crime scene evidence such as blood or other tissues.

A technique often used in such genotypic analysis is known as DNA fingerprinting. This technique relies on the digestion of the DNA of an organism, tissue or cell with a restriction endonuclease enzyme which cleaves the DNA sample into fragments of discrete length. Due to the specificity with which different restriction endonucleases cleave their DNA substrates, a given set of enzymes will always produce the same results, in terms of fragment number and size (the term "size" as used herein is defined as the length and/or molecular weight of a given restriction fragment), from a given DNA sample. The restriction fragments may then be resolved by a variety of techniques such as size exclusion chromatography, gel electrophoresis, or attachment to a variety of solid matrices. Most commonly, gel electrophoresis is performed, and the restriction fragments are resolved into a series of bands on the gel via their differential mobilities within the gel (which is inversely related to fragment size). The pattern of these bands within the gel is specific for a given DNA sample, and is often referred to as the "fingerprint" of that sample.

When the DNA fingerprints of closely related organisms, tissues or even cells are compared, these fingerprints are often quite similar. However, subtle differences between the fingerprints may be observed. These differences, termed "DNA polymorphisms," tend to increase in number (i.e., the fingerprints become more dissimilar) as DNA samples from more distantly related or unrelated organisms are compared. This technique of examining such Restriction Fragment Length Polymorphisms, or "RFLPs," has been used for a number of years in genotypic analysis of eukaryotes such as plants (Tanksley, S. D. et al., *Bio/Technology* 7:257–264 (1989)) and animals, including humans (Botstein, D. et al., *Am. J. Hum. Genet.* 32:314–331 (1980)). In fact, RFLP analysis is being used in combination with other techniques in molecular biology to determine the complete structure (i.e., the "map") of the human genome (See, e.g., Donis-Keller, H. et al., *Cell* 51:319–337 (1987)). In this way, RFLP analysis can be used to determine the relationship, or lack thereof, between specific organisms, tissues or cells by a simple comparison of differences in their DNA fingerprints.

DNA Amplification

One early drawback to the use of RFLP analysis, however, was its requirement for larger amounts of DNA than are typically available in the samples to be analyzed. In addition, complex genomic samples are often difficult to analyze by RFLP, as a multitude of different DNA molecules are simultaneously fragmented and resolved. As a means of overcoming these difficulties, investigators have increasingly turned to methods that increase the copy number of, or "amplify," specific sequences of DNA in a sample.

A commonly used amplification technique is the Polymerase Chain Reaction ("PCR") method invented by Mullis and colleagues (U.S. Pat. Nos. 4,683,195; 4,683,202; and 4,800,159). This method uses "primer" sequences which are complementary to opposing regions on the DNA sequence to be amplified. These primers are added to the DNA target sample, along with a molar excess of nucleotide bases and a DNA polymerase (e.g., Taq polymerase), and the primers bind to their target via base-specific binding interactions (.ie., adenine binds to thynine, cytosine to guanine). By repeatedly passing the reaction mixture through cycles of increasing and decreasing temperatures (to allow dissociation of the two DNA strands on the target sequence, synthesis of complementary copies of each strand by the polymerase, and re-annealing of the new complementary strands), the copy number of a particular sequence of DNA may be rapidly increased.

Other techniques for amplification of target nucleic acid sequences have also been developed. For example, Walker et al. (U.S. Pat. No. 5,455,166; EP 0 684 315) described a method called Strand Displacement Amplification (SDA), which differs from PCR in that it operates at a single temperature and uses a polymerase/endonuclease combination of enzymes to generate single-stranded fragments of the target DNA sequence, which then serve as templates for the production of complementary DNA (cDNA) strands. An alternative amplification procedure, termed Nucleic Acid Sequence-Based Amplification (NASBA) was disclosed by Davey et al. (U.S. Pat. No. 5,409,818; EP 0 329 822). Similar to SDA, NASBA employs an isothermal reaction, but is based on the use of RNA primers for amplification rather than DNA primers as in PCR or SDA.

PCR-based DNA Fingerprinting

Despite the availability of a variety of amplification techniques, most DNA fingerprinting methods rely on PCR for amplification, taking advantage of the well-characterized protocols and automation available for this technique. Examples of these PCR-based fingerprinting techniques include Random Amplified Polymorphic DNA (RAPD) analysis (Williams, J. G. K. et al., *Nucl. Acids Res.* 18(22) :6531–6535 (1990)), Arbitrarily Primed PCR (AP-PCR; Welsh, J., and McClelland, M., *Nucl. Acids Res.* 18(24) :7213–7218 (1990)), DNA Amplification Fingerprinting (DAF; Caetano-Anolles et al., *Bio/Technology* 9:553–557 (1991)), and microsatellite PCR or Directed Amplification of Minisatellite-region DNA (DAMD; Heath, D. D. et al., *Nucl. Acids Res.* 21(24):5782–5785 (1993)). All of these methods are based on the amplification of random DNA fragments by PCR, using arbitrarily chosen primers. The utility of these techniques is limited, however, by their extreme sensitivity to the quality of the target DNA, which may be poor in some genomic or cDNA library samples. Use of poor-quality (e.g., fragmented, degraded or otherwise non-intact) DNA in these techniques can lead, for example, to spurious results due to incomplete amplification of desired target DNA sequences.

More recently, a technique named Amplification Fragment Length Polymorphism (AFLP) analysis was developed by Vos and colleagues (EP 0 534 858; Vos, P. et al., *Nucl. Acids Res.* 23(21):4407–4414 (1995)). This technique, which is also PCR-based, uses specific combinations of restriction endonucleases and adapters of discrete sequences, as well as primers that contain the common sequences of the adapters. In this way, a sequence or fragment of DNA in a complex sample may be specifically amplified and used for further analysis. The value of AFLP in genomic analyses of certain plant and bacterial strains has been demonstrated (Lin, J.-J., and Kuo, J., *Focus* 17(2) :66–70 (1995); Lin, J.-J., et al, *Plant Molec. Biol. Rep.* 14(2):156–169 (1996)), while others have used AFLP for HLA-DR genotyping in humans (Yunis, I. et al., *Tissue Antigens* 38:78–88 (1991)).

Identification of Tissue-Specific cDNAs and Genomic Genetic Markers

Despite the success of genetic mapping using the foregoing techniques, however, these methods are limited in their abilities to identify source-specific DNA sequences. This limitation is particularly true for those sequences derived from genomic DNA samples from different cells, tissues or organisms, and for those derived from tissue cDNA libraries which comprise only those DNA molecules that are actively expressed (i.e., used to make proteins) in the particular tissue and which are thus a subset of genomic DNA. For cDNA libraries, however, methods have been developed that overcome these limitations to some extent.

One such method, termed differential hybridization, relies on the knowledge that specific genes are expressed differentially in certain cells or tissues as opposed to other cells or tissues. To identify these cell- or tissue-specific genes, one can simply prepare cDNAs from two different cell or tissue types and separately hybridize the cDNA samples to oligonucleotide probes prepared from each of the samples. The resultant hybridization patterns can then be compared, and any differences observed indicate the cell- or tissue-specific expression of one or more genes (and thus the presence, in a cDNA library prepared from that cell or tissue, of a specific cDNA). This technique was used to identify growth factor-regulated genes that are specifically expressed in cells stimulated to grow by treatment with serum but that are not expressed in quiescent cells (Lau, H. F., and Nathans, D., *EMBO J* 4:3145–3151 (1985)).

A second, somewhat more sensitive, technique for identifying tissue-specific DNAs is the use of subtractive libraries (See Hedrick, S. M. et al., *Nature* 308:149–153 (1984);

Lin, J.-J., et al., FOCUS 14(3):98–101 (1993)). In this method, cDNAs prepared from the one tissue or cell type are mixed with the mRNAs from another, closely related, tissue or cell type. The cDNAs that are expressed in both cells or tissues then form DNA-RNA hybridization complexes, since they are complementary to each other, while the cDNAs expressed selectively in one cell/tissue but not the other will not form such a complex. The DNA-RNA complexes, representing cDNAs that are not tissue-specific, can then be removed from the mixtures (i.e., "subtracted") by passing the mixture through a poly-dT or hydroxyapatite column, to which the unhybridized cDNAs will not bind. This procedure thus results in a purified sample that is enriched in tissue- or cell-specific cDNAs.

Amplification-Based Cloning

While differential hybridization and the use of subtractive libraries may be suitable for the identification of DNA sequences that are expressed at relatively high levels in the source cells or tissues, they are not particularly useful when the starting samples contain only low levels of genomic DNA (or mRNA used to make cDNAs). This problem is particularly important when the tissue or cell samples are themselves present in low quantities (as in many medical or forensic applications), or when the specific DNA sequence is expressed at low levels in the cell/tissue samples.

PCR-based cloning of tissue-specific cDNAs has been used in the attempt to overcome the lack of sensitivity of earlier approaches (see, e.g., Lee, C. C., et al., *Science* 239:1288–1291 (1988)). However, this approach still suffers from the major shortcoming of PCR itself—the requirement for prior knowledge of the nucleotide sequence of the DNA to be amplified, to allow construction of complementary PCR primers. Without knowing the nucleotide sequence of the target DNA, PCR cannot be performed in order to amplify this sequence in the sample. Since the target sequences are not known in many medical or forensic samples, PCR-based cloning is not useful for the identification or isolation of tissue-specific cDNAs from these samples. For the same reasons, these techniques are not suitable for the identification of previously unknown or uncharacterized genes from cDNA libraries or genomic samples. Furthermore, as noted above, the complexity of genomic DNA limits the utility of these techniques in the identification and isolation of genetic markers from the genome of a cell or organism.

Thus, there remains an unmet need for a rapid, reproducible and reliable technique for identifying fragments of DNA, or genes, that are unique to the genomes of specific organisms, tissues or cells, or that are unique to cDNA libraries prepared from these specific sources, without prior knowledge of the nucleotide sequence of the unique DNA fragments. Particularly desirable are methods that would rapidly identify, and allow the isolation of, specific DNA sequences found in one source cDNA library or genome but not in another library or genome. Such a technique would find utility in a variety of applications, particularly in clinical, forensic and plant breeding applications.

BRIEF SUMMARY OF THE INVENTION

The present invention is directed to AFLP-based methods that address these unmet needs. In particular, the invention relates to such methods that allow the identification and isolation of tissue-specific cDNAs from cDNA libraries, or the identification and isolation of specific genetic markers from samples of genomic DNA.

In one embodiment, the invention is directed to a method for identifying a cDNA fragment from a first cDNA library which is not present in a second cDNA library, comprising the steps of (a) digesting a first and second cDNA library with at least one restriction enzyme to give a collection of restriction fragments, and (b) identifying one or more unique fragments from the first cDNA library by comparing the fragments from the first cDNA library to fragments from the second cDNA library.

In another embodiment, the invention is directed to a method for identifying a genetic marker, comprising a DNA fragment from a first sample of genomic DNA, which is not present in a second sample of genomic DNA. This method comprises the steps of (a) digesting the first and second samples of genomic DNA with at least one restriction enzyme to give a collection of restriction fragments, and (b) identifying one or more unique DNA fragments in the first or second samples of genomic DNA by comparing the fragments obtained from one sample of genomic DNA to those obtained from the other sample.

According to the invention, the identifying step in the above methods is preferably accomplished by separating the restriction fragments according to size, which is as used herein is defined as the length and/or molecular weight of the restriction fragments. This aspect of the invention may further comprise sequencing the unique cDNA or genomic DNA fragments, and may entail amplification of the restriction fragments prior to the identifying step (b). In another aspect of the invention, the restriction fragments are detectably labeled. The present invention also encompasses the above method which further comprises the steps of (c) isolating at least one unique fragment, and (d) inserting the fragment into a vector, which may be an expression vector, for use in transfecting or transforming a prokaryotic or eukaryotic host cell; the fragment may be amplified prior to insertion into the vector. In another aspect of this embodiment, the unique fragment may be sequenced according to routine nucleotide sequencing methods.

In another embodiment, the present invention provides a method for isolating a cDNA from a first cDNA library, comprising the steps of (a) mixing one or more of the unique fragments identified as summarized above, or one or more oligonucleotide probes which are complementary to the fragments, with a first cDNA library under conditions stringent for hybridization of the unique fragments or oligonucleotide probes to the first cDNA library; and (b) isolating a cDNA which is complementary to the unique fragments or to the oligonucleotide probes. Analogously, the invention also provides a method for isolating a genetic marker, comprising a DNA fragment, from a sample of genomic DNA. This method comprises the steps of (a) mixing one or more of the unique fragments identified as summarized above, or one or more oligonucleotide probes which are complementary to the fragments, with a sample of DNA under conditions stringent for hybridization of the unique fragments or oligonucleotide probes to the sample of DNA; and (b) isolating a DNA fragment which is complementary to the unique fragments or to the oligonucleotide probes.

According to the present invention, the isolation steps (b) of the above-described methods may be accomplished by gel electrophoresis, density gradient centrifugation, sizing chromatography, affinity chromatography, immunoadsorption, or immunoaffinity chromatography. In this embodiment, the isolated CDNA or DNA fragments may also be sequenced, amplified, or inserted into a vector (which may be an expression vector). DNA fragments isolated by this embodiment of the present invention will be useful in, for example, the preparation of DNA or RNA probes, and to aid in a variety of medical, forensic, industrial and plant breeding applications.

The invention also encompasses the methods described above, wherein the amplification of the unique cDNA or genomic DNA fragments is accomplished by a method comprising the steps of (a) ligating one or more adapter oligonucleotides to a unique cDNA fragment or genomic DNA fragment to form a DNA-adapter complex; (b) hybridizing the DNA-adapter complex, under stringent conditions, with one or more oligonucleotide primers which are complementary to the adapter portion of the DNA-adapter complex to form a hybridization complex; and (c) ampliiying the DNA-adapter complex. In this aspect of the invention, the adapter oligonucleotide may contain one or more restriction sites which may be used to insert the DNA-adapter complex into a vector.

According to the present invention, the first and second cDNA libraries or samples of genomic DNA used in the above-described methods may be derived from an individual cell (which may be prokaryotic or eukaryotic), a tissue (which may be a plant or an animal tissue, most preferably a human tissue including a human embryonic or fetal tissue), an organ, or a whole organism. The genetic marker identified according to this embodiment of the invention may be a cancer marker, an infectious disease marker, a genetic disease marker, a marker of embryonic development, a tissue-specific marker or an enzyme marker. In one such aspect of the invention, one cDNA library or sample of genomic DNA may be derived from an animal suffering from an infectious disease (e.g., a disease of bacterial, fungal, viral or parasitic origin) and the other cDNA library or sample of genomic DNA may be from an animal not suffering from an infectious disease. In another aspect, one cDNA library or sample of genomic DNA may be derived from an animal suffering from cancer and the other may be derived from an animal not suffering from cancer. In another aspect, one cDNA library or sample of genomic DNA may be obtained from a cancerous animal tissue and the other from a noncancerous animal tissue, which tissues may both be obtained from the same animal. In another aspect, one cDNA library or sample of genomic DNA may be from an animal suffering from a genetic disease and the other may be derived from an animal not suffering from a genetic disease. In another aspect, one cDNA library or sample of genomic DNA may be derived from a pathogenic microorganism and the other from a non-pathogenic organism. In another aspect, one cDNA library or sample of genomic DNA may be derived from an organism expressing an enzyme, and the other sample may be derived from an organism not expressing an enzyme. In another aspect, one cDNA library or sample of genomic DNA may be derived from an organism expressing an industrially useful protein, and the second may be derived from an organism not expressing an industrially useful protein. In another aspect, one cDNA library or sample of genomic DNA may be derived from a diseased plant and the other sample may be derived from a non-diseased plant. In another aspect, one cDNA library or sample of genomic DNA may be from a plant resistant to an environmental stress, which may be drought, excess temperature, diminished temperature, chemical toxicity by herbicides, pollution, excess light or diminished light, and the other sample may be from a plant not resistant to an environmental stress.

In another embodiment, the present invention provides a method of determining the relationship between a first individual and a second individual comprising the steps of (a) digesting a cDNA library or a sample of genomic DNA obtained from the first and second individuals with at least one restriction enzyme to give a collection of restriction fragments; (b) separating the restriction fragments from the first and second individuals according to size; and (c) determining the similarities and dissimilarities of the sizes or concentrations of the restriction fragments separated in step (b). In a preferred aspect of this embodiment, this comparison is accomplished by computer analysis.

Other preferred embodiments of the present invention will be apparent to one of ordinary skill in light of the following drawings and description of the invention, and of the claims.

DETAILED DESCRIPTION OF THE INVENTION

The present invention provides a method for identifying and isolating unique DNA fragments or genes from genomic DNA samples. It will be readily appreciated by those skilled in the art that using the methods of this invention, any genomnic DNA fragment comprising a sequence of contiguous nucleotide bases that is specifically contained within a given host genome may be identified and isolated.

Sources of cDNA Libraries and Genomic DNA cDNA libraries and genomic DNA, as well as sources from which cDNA libraries and genomic DNA may be prepared, are available commercially from a number of sources, including Life Technologies, Inc. (Rockville, Md.), American Type Culture Collection (ATCC; Rockville, Md.), Jackson Laboratories (Bar Harbor, Me.), Cell Systems, Inc. (Kirkland, Wash.) and Advanced Tissue Sciences (La Jolla, Calif.). Cells that may be used as starting materials for cDNA and genomic DNA preparation may be prokaryotic (bacterial, including members of the genera Escherichia, Serratia, Salmonella, Staphylococcus, Streptococcus, Clostridium, Chlamydia, Neisseria, Treponema, Mycoplasma, Borrelia, Bordetella, Legionella, Pseudomonas, Mycobacterium, Helicobacter, Agrobacterium, Collectotrichum, Rhizobium, and Streptomyces) or eukaryotic (including fungi or yeasts, plants, protozoans and other parasites, and animals including humans and other mammals). Any mammalian somatic cell may also be used for preparation of cDNA libraries and genomic DNA, including blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells. Mammalian germ cells. (spermatocytes and oocytes) may also be used for the preparation of cDNA libraries and genomic DNA, as may the progenitors, precursors and stem cells that give rise to the above-described somatic and germ cells. Also suitable for use in the preparation of cDNA libraries and genomic DNA are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus. These cells, tissues and organs may be normal, or they may be pathological such as those involved in infectious diseases (caused by bacteria, fungi or yeast, viruses (including HIV) or parasites), in genetic or biochemical pathologies (e.g., cystic fibrosis, hemophilia, Alzheimer's disease, schizophrenia, muscular dystrophy or multiple sclerosis), or in cancerous processes.

The methods of the invention may comprise one or more steps. For example, the invention is directed to a method for identifying a DNA fragment from a first cDNA library or sample of genomic DNA, which fragment is not present in a second cDNA library or sample of genomic DNA, comprising:

(a) digesting the first and second cDNA libraries or samples of genomic DNA with at least one restriction enzyme to give a collection of restriction fragments; and (b) identifying one or more unique fragments from the first cDNA library or sample of genomic DNA by comparing the fragments from the first cDNA library or sample of genomic DNA to the fragments from the second cDNA library or sample of genomic DNA Analogously, the invention is directed to a method for identifying a DNA fragment from a second cDNA library or sample of genomic DNA, which fragment is not present in a first cDNA library or sample of genomic DNA, comprising: (a) digesting the first and second cDNA libraries or samples of genomic DNA with at least one restriction enzyme to give a collection of restriction fragments; and (b) identifying one or more unique fragments from the second cDNA library or sample of genomic DNA by comparing the fragments from the second cDNA library or sample of genomic DNA to the fragments from the first cDNA library or sample of genomic DNA.

In one aspect of the invention, one cDNA library or sample of genomic DNA may be derived from a sample from an animal suffering from an infectious disease (e.g., a disease of bacterial, fungal, viral or parasitic origin) and the other sample of genetic may be from an animal not suffering from an infectious disease. In another aspect, one cDNA library or sample of genomic DNA may be derived from an animal suffering from cancer and the other may be derived from an animal not suffering from cancer. In another aspect, one cDNA library or sample of genomic DNA may be obtained from a cancerous animal tissue and the other may be obtained from a noncancerous animal tissue, which tissues may both be obtained from the same animal. In another aspect, one cDNA library or sample of genomic DNA may be from an animal suffering from a genetic disease and the other cDNA library or sample of genomic DNA may be from an animal not suffering from a genetic disease. In another aspect, one cDNA library or sample of genomic DNA may be obtained from a pathogenic microorganism and the other library or sample may be obtained from a non-pathogenic microorganism. In another aspect, one cDNA library or sample of genomic DNA may be derived from an organism expressing an enzyme, and the other may be derived from an organism not expressing an enzyme. Particularly preferred in this aspect of the invention are cDNA libraries and samples of genomic DNA from organisms with differential expression of a restriction enzyme, an enzyme degrading a petroleum product, a biodegradative enzyme, a nucleic acid polymerase enzyme, a nucleic acid ligase enzyme, an amino acid synthetase enzyme and an enzyme involved in carbohydrate fermentation; it is to be understood, however, that CDNA libraries or samples of genomic DNA from organisms with differential expression of any enzyme may be used in the methods of the present invention. In another aspect, one cDNA library or sample of genomic DNA may be derived from an organism expressing an industrially useful protein, and the second may be derived from an organism not expressing an industrially useful protein. Particularly preferred in this aspect of the invention are cDNA libraries and samples of genomic DNA from organisms with differential expression of proteins used in food and beverage manufacturing (e.g., enzymes, flavorings, preservatives, bulking agents and the like), and those used in chemical and pharmaceutical manufacturing (particularly enzymes, cofactors, carriers, immunogens, preservatives, bulking agents and the like). In another aspect, one cDNA library or sample of genomic DNA may be derived from a diseased plant and the other may be derived from a non-diseased plant. In another aspect, one cDNA library or sample of genomic DNA may be from a plant resistant to an environmental stress, which may be drought, excess temperature, diminished temperature, chemical toxicity by herbicides, pollution, excess light or diminished light, and the other may be from a plant not resistant to an environmental stress. Other suitable sources of cDNA libraries and samples of genomic DNA will be apparent to one of ordinary skill.

Once the starting cells, tissues, organs or other samples are obtained, cDNA libraries and genomic DNA may be prepared therefrom by methods that are well-known in the art (See, for example, Maniatis, T. et al., *Cell* 15:687–701 (1978); Okayama, H., and Berg, P., *Mol. Cell. Biol.* 2:161–170 (1982); Gubler, U., and Hoffthan, B. J., *Gene* 25:263–269 (1983); Maniatis, T., et al., *Molecular Cloning: A Laboratory Manual*, Cold Spring Harbor, N.Y.: Cold Spring Harbor Laboratory Press, pp. 9.16–9.23 (1989); Kaufian, P. B., et al., *Handbook of Molecular and Cellular Methods in Biology and Medicine*, Boca Raton, Fla.: CRC Press, pp. 1–26 (1995), the disclosures of which are incorporated herein by reference in their entireties). The cDNA libraries and genomic DNA samples thus prepared, or those obtained from commercial sources, may then be used to identify and isolate unique cDNA and genoric DNA fragments (i.e., tissue-specific fragments or genetic markers) by the methods of the present invention.

Purification of cDNA

Having obtained cDNA libraries from various tissues, either from commercial sources or by preparation as taught above, the cDNA molecules are purified in preparation for analysis by AFLP. Detailed methodologies for purification of cDNAs are taught in the GENETRAPPER™ manual (LTI; Gaithersburg, Md.), which is incorporated herein by reference in its entirety. Bacterial hosts (*E. coli* is commonly used, although another suitable bacterial or yeast host may also be used) containing therein plasmids comprising cDNAs of interest are grown in culture at an appropriate temperature (30–37° C., depending upon the specific bacterial host used) overnight, preferably for 12–24 hours, and most preferably for 18–24 hours. Any culture medium promoting rapid growth of the host cells is suitable for use, although a tryptone-based broth culture is preferred and most preferred is TBG broth containing 1–2% tryptone, 2–5% yeast extract, 0.1–1% glycerol, 10–50 mM glucose, and concentrations of buffer salts that are standard in the art. Such culture media are available commercially, for example from GIBCO/BRL (Gaithersburg, Md.).

After growth, culture broth containing host cells is transferred to sterile centrifuge containers (tubes or bottles) and is centrifuged at 10,000–20,000×g, most preferably at 16,000×g, for 10–15 minutes at 4° C. Supernatants are then completely removed, by aspiration or pouring off, taking care not to dislodge, resuspend or otherwise disturb pelleted host cells in the bottoms of the centrifuge containers.

Host cell pellets are then subjected to a procedure to liberate plasmids containing cDNAs. Procedures commonly used to perform this task include the use of lysozyme and physical pressure (the "French Press"), freeze-thawing, or sonication; these procedures, however, will often lead to shearing or fragmenting of target cDNAs which is undesirable. A more preferred method to free cDNA-containing plasmids from host cells is via alkaline lysis of the host cells, as it results in less degradation of the target cDNA molecules. In this method, cell pellets are resuspended in a low ionic strength buffer containing an alkali salt and a detergent. For example, a volume of a solution (hereinafter "TE buffer") containing about 50 mM glucose, about 50 mM TRIS®-HCl (pH 8.0), and about 10 mM disodium ethylenediaminetetraacetate (EDTA) is most preferably used for resuspension of cell pellets. Two volumes of alkaline-detergent solution are then added to this cell suspension to promote lysis of the host cells and liberation of cDNAs; most preferable for this step is a solution of about 0.2 N sodium hydroxide and about 1% sodium dodecylsulfate, although any alkaline-detergent solution of approximately equivalent pH and ionic strength may be used.

After addition of the alkaline-detergent solution, the suspension in the centrifuge container is thoroughly mixed and then incubated at 0–4° C. (preferably in an ice bath) for approximately five minutes. Following this incubation, the lysis solution is neutralized by the addition of an acid salt; addition of ½ volume of about 3M potassium acetate (pH 4.8) is preferred with the above alkaline-detergent solution, although any acid salt of equivalent pH and ionic strength may also be used. The solution in the centrifuge container is then gently mixed and centrifuged under the same conditions as described above for pelleting the cells, to remove cellular debris from cDNA-containing plasmids which remain in the supernatants.

Supernatants are then withdrawn (and pellets discarded) and transferred to a fresh, sterile container. To effectuate precipitation of cDNAs, two volumes of absolute ethanol are added to the supernatants, and the mixtures are then incubated for 5–30 minutes, preferably for 10–15 minutes, at –20° to –70° C., most preferably in a bath containing dry ice and ethanol. The mixtures are then centrifuged (again as above) to pellet precipitated cDNAs. Supernatants are removed by aspiration, again taking care to prevent disruption of the pellets, and pellets are resuspended in a buffer solution, preferably a solution containing about 10 mM TRIS®-HCl (pH 8.0) and about 1 mM EDTA.

The ethanol precipitation step described above will also result in the precipitation of RNA molecules from the host cell, which will interfere with subsequent amplification and analysis of tissue-specific cDNAs. To remove these unwanted RNAs, the samples may be treated with an RNA-degrading enzyme such as RNase A (available commercially, for example, from GIBCO/BRL, Gaithersburg, Md.), which must be substantially free of contaminating DNase enzymes to prevent degradation of the target cDNAs. Following treatment with RNase A, cDNAs are isolated by extracting the solutions with phenol, reprecipitation with ethanol and recentrifugation, according to methods that are well-known in the art (Lin and Kuo, Focus 17(2):66–70 (1995)). The final pellets, containing purified cDNAs, are then used for AFLP analysis.

Identification of Tissue-Specific cDNAs and Genetic Markers

Purified cDNA and genomic DNA may be examined by AFLP for identification of specific (including tissue-specific) cDNAs or genetic markers according to the present invention. AFLP was originally developed as a method for DNA fingerprinting analysis of bacterial, yeast, plant and animal cells (EP 0 534 858; Vos, P., et al., *Nucl Acids Res.* 23(21):4407–4414 (1995); Lin, J.-J., and Kuo, J., *FOCUS* 17(2):66–70 (1995); Lin, J.-J., et al., *Plant Molec. Biol. Rep.* 14(2):156–169 (1996)). In the present invention, the AFLP technique has been modified to provide, in one embodiment, a method for identifying a tissue-specific cDNA from a cDNA library, or a genetic marker from a sample of genomic DNA and, in another embodiment, a method for isolating these specific cDNAs or genetic markers.

AFLP may be carried out using a commercially available system such as the AFLP Analysis System I (Life Technologies, Inc.; Rockville, Md.) which contains a detailed methods manual, the disclosure of which is fully incorporated herein by reference. Alternatively, AFLP analysis may be performed using a combination of materials and methods that are modified from those commonly used in the art (Vos, P., et al., *Nucl. Acids Res.* 23(21):4407–4414 (1995); Lin, J.-J., and Kuo, J., *FOCUS* 17(2):66–70 (1995); Lin, J.-J., et al, *Plant Molec. Biol Rep.* 14(2):156–169 (1996)).

The power of the AFLP technique is based on its use of generic primers and "adaptors" which allow amplification of DNA fragments without any prior knowledge of the nucleotide sequences of those fragments. In this way, the AFLP-based method of the present invention is more useful for identification of previously unknown tissue-specific cDNAs, and genomic genetic markers, than is traditional PCR which requires prior knowledge of the nucleotide sequence of the target DNA in order to design appropriate amplification primers.

In the initial step of AFLP, purified cDNA or genomic DNA is digested with a panel of enzymes usually containing two restriction enzymes. Ordinarily, the two restriction enzymes have sequence specificities sufficiently different from one another so as to prevent overlap of digestion (and thus over-degradation) of the target DNA sequences. For example, the enzymes EcoRI and MseI may be used in combination to digest target DNA, as the restriction site specificities of these two enzymes are significantly different. However, other combinations of restriction enzymes may be used in carrying out the present invention with equal likelihood of success.

Once the cDNA or genomic DNA has been digested with restriction enzymes (producing "restriction fragments," hereinafter referred to as "RFs"), the resultant RFs are ligated with adaptor sequences which extend the region on the RFs to which the PCR primers will bind during amplification, thus forming DNA-adaptor complexes. The use of adaptors is necessary since after digestion, the cut ends of the RFs, to which the PCR primers will bind, are often too short for optimal binding of the primers. Accordingly, ligation of adaptor sequences to the cut ends of the RFs extends the length of these primer binding sites, improving the efficiency of primer binding and thus of amplification. The nucleotide sequences of these adaptors are chosen so as to contain the nucleotide sequences at the restriction sites in the target cDNA or genomic DNA samples. The adaptors usually will have a stretch of 2–8 contiguous nucleotides which are complementary to the cut ends of the RFs; thus, the adaptors bind to the RFs via normal DNA base-pairing and thereby extend the terminal sequence of the RFs.

Once the adaptors have been ligated to the DNA RFs, the fragments are amplified via PCR according to standard methods used for cDNA fragment amplification (Lin, J.-J., and Kuo, J., *FOCUS* 17(2):66–70 (1995)), using PCR primer oligonucleotides that hybridize to the adaptor portions of the DNA-adaptor complexes (i.e., the binding regions of the primers are complementary to the sequences of the adaptors) under conditions used for PCR. This approach provides the additional advantage that the actual sequences of the cDNA or genomic DNA fragments that are the targets for amplification need not be known, since the primers are designed to be specific for a restriction site rather than a particular gene. Accordingly, generic primers may be used, with their nucleotide sequences being dependent upon the combination of restriction enzymes used to digest the target cDNAs or genomic DNAs, as has been described for cDNAs (Vos, P., et al, *Nucl. Acids Res.* 23(21):4407–4414 (1995); Lin, J.-J., and Kuo, J., *FOCUS* 17(2):66–70 (1995); Lin, J.-J., et al., *Plant Molec. Biol. Rep.* 14(2):156–169 (1996)). For example, EcoRI primers contain the sequence of the EcoRI restriction site (underlined below) coupled to core sequences and arbitrary extenders of three-base repeat units:

5'-CAU CAU CAU CAU GAC TGC GTA CCA ATTC-3'
 [(CAU$_4$)EcoRI+0] primer (SEQ ID NO: 1)
5'-GAC TGC GTA CCA ATT CAC C-3'
 [EcoRI+ACC] primer (SEQ ID NO: 2)

Similarly, the MseI primers will contain the nucleotide sequence of the MseI restriction site linked to different core and extender sequences:

5'-CUA CUA CUA CUA GAT GAG TCC TGA GTA A-3'
 [(CUA$_4$)MseI+0] primer (SEQ ID NO: 3);
5'-GAT GAG TCC TGA GTA ACA A-3'
 [MseI+CAA] primer (SEQ ID NO: 4); or
5'-GAT GAG TCC TGA GTA ACA C-3'
 [MseI+CAC] primer (SEQ ID NO:5).

These primers may be detectably labeled, preferably with a radioisotope of phosphorus ($^{32}$p or $^{33}$P), although other detectable labels such as fluorophors or phosphors, enzymes, or biotin/avidin may be used as well.

Following amplification, the samples are prepared for separation of the DNA fragments, a procedure which permits the determination of the expression of tissue- or cell-specific cDNAs in the cDNA libraries, or the presence of specific genetic markers in the genomic DNA samples. The fragments may be separated by any physical or biochemical means including gel electrophoresis, chromatography (including sizing, affinity and immunochromatography), density gradient centrifugation and immunoadsorption. In the practice of the present invention, separation of DNA fragments by gel electrophoresis is particularly preferred, as it provides a rapid and highly reproducible means of sensitive separation of a multitude of DNA frents, and permits direct comparison of the fragments in several CDNA libraries or samples of genomic DNA simultaneously.

Gel electrophoresis is typically performed on agarose or polyacrylamide sequencing gels according to standard protocols (Lin, J.-J., and Kuo, J., *FOCUS* 17(2):66–70 (1995)), preferably using gels containing polyacrylamide at concentrations of 3–8% and most preferably at about 5%, and containing urea at a concentration of about 8M. Samples are loaded onto the gels, usually with samples containing cDNAs or genomic DNA fragments prepared from different sources being loaded into adjacent lanes of the gel to facilitate subsequent comparison.

Following electrophoretic separation, DNA fragments may be visualized and identified by a variety of techniques that are routine to those of ordinary skill in the art. In a first such technique, the gel is dried using a commercial gel dryer and exposed to X-ray (for detection of radioisotopes) or high-sensitivity photographic (for detection of fluorophors or phosphors) film. After development, the film is examined for the pattern of bands in each lane of the gel, each band corresponding to a different DNA species or fragment (see FIGS. 1–5). The migration of DNA fragments within the gel is proportional to their size (length and/or molecular weight)—i.e., larger fragments migrate more slowly (and thus form bands closer to the top of the gel), while smaller fragments migrate more quickly (and thus form bands closer to the gel bottom). One can thus examine the films for the presence of one or more unique bands in one lane of the gel (see arrows in FIGS. 1–4); the presence of a band in one lane (corresponding to a single sample, cell or tissue type) that is not observed in other lanes indicates that the DNA fragment comprising that unique band is source-specific and thus a potential tissue- or cell-specific cDNA or genomic genetic marker.

Alternatively, DNA fragments may be visualized by staining the gel with a nucleic acid-binding stain such as ethidium bromide or silver stain. The DNA fragments are then visualized by illumination of the gel with a wavelength range of light specific for the stain used, e.g. UV illumination for ethidium bromide or visible light for silver stain.

Isolation and Characterization of Tissue-Specific cDNAs and Genomic Genetic Markers A variety of tissue-specific cDNAs and genomic DNA fragments comprising genetic markers can thus be identified using the methods of the present invention by comparing the pattern of bands on the films depicting various samples. One can extend this approach, in another embodiment of the invention, to isolate and characterize these genetic markers. In this embodiment, one or more of the specific DNA fragments are removed from the dried gel which was used for identification (see above). Removal of these fragments from the gel may be effected by a number of means including electroelution or preferably by physical excision. This excision is preferably accomplished by overlaying the developed film (autoradiogram) directly over the dried gel, thus allowing the developed film to be used as a guide or template to localize the fragments of interest in the gel. The fragments represented by unique bands on the autoradiogram may then be carefully cut from the dried gel through the corresponding band on the film using, for example, a scalpel, razor or scissors. The DNA is then eluted from the gel by incubating the slice for about 18–24 hours at 37° C. in TE buffer. Following elution, the DNA sample in TE buffer is loaded into a syringe containing sterilized glass wool and filtered through the glass wool into a sterile tube via centrifugation at about 250–500×g for about 10 minutes at about 20–25° C. Alternatively, this filtration may be accomplished via other chromatographic methods that are well known in the art, such as using standard glass wool columns and peristaltic pumping. After being filtered through glass wool, the DNA-containing sample is filtered through a desalting/buffer exchange column (e.g., using SEPHADEX® or a pre-packed PD-10 column available from Pharmacia, Piscataway, N.J.) according to the manufacturer's instructions. This desalting/buffer exchange step may be accomplished by other methods routine in the field, e.g., via batch dialysis, although the use of columns for this purpose overcomes the longer time required, higher cost and sample loss that often accompany standard dialysis methods. The unique cDNA or genomic DNA fragments may then be eluted from the desalting column in deionized, distilled water and lyophilized and stored at 4° C. to −70° C. until use. Alternatively, these AFLP-defined, tissue-specific fragments or genetic markers can be immediately dissolved in TE buffer and re-amplified as outlined above to increase their concentration. Prior to or following this amplification, the unique cDNA or genomic DNA fragments may be inserted into standard nucleotide vectors (such as expression vectors) suitable for transfection or transformation of a variety of prokaryotic (bacterial) or eukaryotic (yeast, plant or animal including human and other mammalian) cells.

Use of Unique cDNA and Genomic DNA Fragments

The tissue- or cell-specific cDNAs, or genomic DNA fragments comprising genetic markers, that are identified and isolated by the methods of the present invention may be further characterized, for example by cloning and sequencing (i.e., determining the nucleotide sequences of the cDNA or genomic DNA fragments), by methods described above and others that are standard in the art (see also U.S. Pat. Nos. 4,962,022 and 5,498,523, which are directed to methods of DNA sequencing). Alternatively, these fragments may be used for the manufacture of various materials in industrial processes, such as hybridization probes or therapeutic proteins (dependent upon transcription and translation of the DNA fragments, or the production of synthetic peptides or proteins with amino acid sequences deduced from the nucleotide sequences of the specific cDNAs or genetic markers) by methods that are well-known in the art. Production of hybridization probes from tissue-specific cDNAs and unique genoric DNA fragments will, for example, provide the ability for those in the medical field to examine a patient's cells or tissues for the presence of a particular genetic marker such as a marker of cancer, of an infectious or genetic disease, of a marker of embryonic development, or of a tissue-specific marker. Particularly suitable for diagnosis by the methods of the present invention are genetic diseases such as cystic fibrosis, hemophilia, Alzheimer's disease, schizophrenia, muscular dystrophy or multiple sclerosis. Also suitable for identification by the methods of the present invention are genetic markers associated with pathogenicity (e.g., virulence genes) of microorganisms. In addition, the presence of genetic markers of schizophrenia in patient samples may be determined by the present methods. Furthermore, such hybridization probes can be used to isolate DNA fragments from genomic DNA or cDNA libraries prepared from a different cell, tissue or organism for further characterization. In this application of the present invention, hybridization probes comprising the AFLP-defined unique fragments identified above, or one or more oligonucleotide probes complementary to these fragments, are hybridized under conditions of stringent hybridization with genomic DNA or a first cDNA library prepared from a cell, tissue or organism, such as any of those described above. As used herein, the term "stringent hybridization conditions" is defined, as is generally understood in the field, as incubation of the genomic DNA or first cDNA library with the hybridization probe(s) for 18–24 hours at about 42° C. in a solution comprising 5X SSC (1X SSC=150 mM NaCl, 15 mM trisodium citrate), 50 mM sodium phosphate (pH about 7.6), 5X Denhardt's solution, 50% formamide, 10% dextran sulfate and 20 g/ml denatured, sheared salmon sperm DNA. Following hybridization, the samples may be washed in 0.1X SSC at about 65° C. to further reduce nonspecific background, and the unique genomic DNA or cDNA fragments so isolated may be amplified and characterized as described above. Together, these abilities will assist medical professionals and patients in diagnostic and prognostic determinations as well as in the development of treatment and prevention regimens for these and other disorders.

It should also be apparent that this method can be used to screen animal tissues to be subsequently used in medical procedures such as tissue or organ transplants, blood transfusions, zygote implantations and artificial inseminations. In such procedures, pre-screening of the subject tissues for the presence of particular genetic markers may improve the success of tissue or organ transplants (by decreasing the likelihood of rejection due to donor-recipient genetic incompatibility) and of zygote implantations (by eliminating the use of genetically defective zygotes). Similarly, use of these methods will reduce the chances of transmission of infectious diseases (e.g., hepatitis and AIDS) in medical procedures that are often prone to such transmission, such as blood transfusions and artificial insemination. Finally, use of the present invention for identification and isolation of unique tissue-specific cDNAs and genomic DNA fragments will assist in forensic science in such applications as crime-scene analysis of blood, tissue and body secretions containing small amounts of DNA, as well as in paternity testing.

It will be readily apparent to one of ordinary skill in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLES
Materials and Methods

The Following Materials and Methods Were Used for All Examples:

Human cDNA libraries of brain, kidney, leukocytes and liver were S purchased from Life Technologies, Inc. (Rockville, Md.). Purification of cDNA was performed by inoculating 1×106 bacterial cells into 100 ml of TB broth in a 250 ml flask, and incubating at 30° C. overnight as described in the GENETRAPPER™ (LTI) manual. Bacterial cells were harvested by centrifugation, and plasmid DNA purified from the resultant bacterial pellets as described (Lin et al., Id). Briefly, cell pellets were suspended in a TRIS-buffered SDS/EDTA solution, incubated on ice to allow disruption of cells, extracted with potassium acetate, and the extract clarified by centrifugation. DNA in clarified supernatants was precipitated with absolute ethanol, pelleted, and resuspended in a TRIS-buffered EDTA (TE) solution. RNA in the samples was degraded with RNase A, and the DNA was extracted with phenol and re-precipitated with ethanol and pelleted by centrifugation at 16,000×g at 4° C. for 10 minutes. Resultant pellets were suspended in TE prior to being used in all experiments.

Genomic DNA was isolated from leukocytes of four pairs of identical twins kindly provided by Dr. Yolken (Johns Hopkins University, Baltimore, Md.). For each pair, one individual was normal while the other was diagnosed as schizophrenic or bipolar.

For analysis of cDNAs and genomic DNA fragments, the Life Technologies, Inc., AFLP Analysis System I (Catalogue No. 10544) was used as described (Lin, J.-J., and Kuo, J., FOCUS 17(2):66–70 (1995)). Briefly, 500 ng of cDNA or genomic DNA, isolated as described above, were digested with EcoRI and MseI, ligated with EcoRI and MseI adapters, and amplified via PCR using $^{32}$P-labeled selective primers for EcoRI (SEQ ID NO:2) and MseI (SEQ ID NOs:4,5) as recommended by the manufacturer. Amplified fragments were separated by polyacrylamide gel electrophoresis, and a unique DNA fragment was sliced from the sequencing gel. This unique fragment was amplified with [(CAU)$_4$EcoRI+0] (SEQ ID NO: 1) and [(CUA)MseI+0] (SEQ ID NO:3) primers, annealed into a pAMP-1 vector, treated with UDG and introduced into transformation-competent E. coli DH10B host cells (Life Technologies, Inc.; Rockville, Md.) by electroporation (Lin, J.-J., et al., FOCUS 14(3):98–101 (1993)). After growth of the cells in selective media containing ampicillin, plasmid DNA was isolated and digested with restriction endonucleases to determine bacterial clones prior to sequencing the plasmid DNA using the dsDNA Cycle Sequencing System (Life Technologies, Inc.; Rockville, Md.) according to manufacturer's instructions.

Example 1

Figure 1:
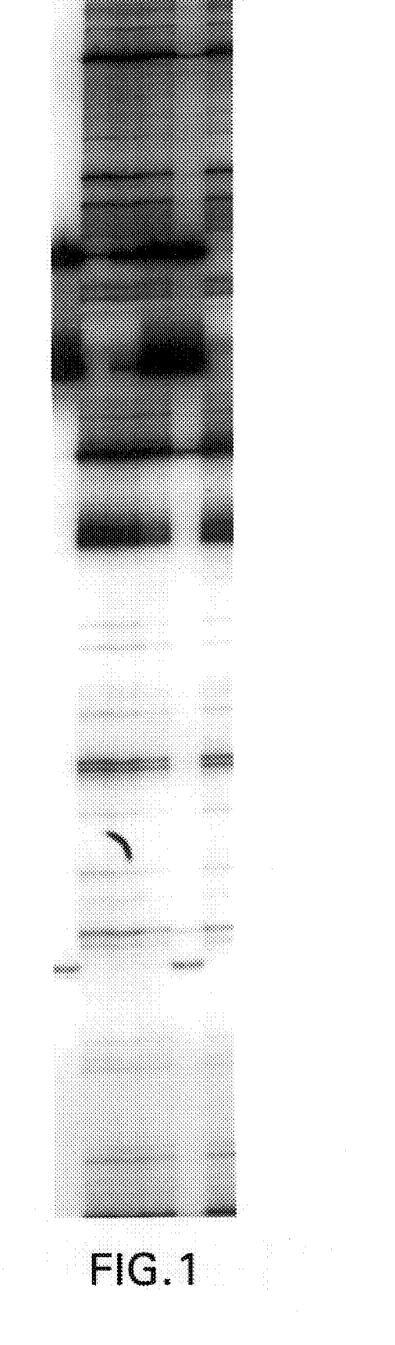
FIG. 1 is an autoradiogram of $^{32}$P-labeled EcoRI/MseI restriction fragments, separated by gel electrophoresis (5% polyacrylamide+8M urea sequencing gel), of samples from a human brain cDNA library (500 nanograms per sample) containing increasing amounts of pCMVSPORTCAT cDNA. Lane 1, pCMVSPORTCAT control (no brain cDNA); Lanes 2–6, 500 ng of human brain cDNA containing the following amounts of pCMVSPORTCAT cDNA: Lane 2: 0.3 ng; Lane 3, 3 ng; Lane 4, 30 ng; Lane 5, 300 ng; Lane 6, 0 ng (brain cDNA control). Arrows indicate pCMVSPORTCAT-specific fragments.

To evaluate the ability of the AFLP-based method of the present invention to identify unique sequences in a cDNA library, different amounts of plasmid pCMVSPORT containing the chloramphenicol resistance gene (pCMVSPORTCAT) were added into 500 ng of cDNA isolated from a human brain cDNA library. AFLP was performed as described above on samples of brain cDNA with or without pCMVSPORTCAT cDNA, and the restriction patterns of these samples determined by gel electrophoresis (FIG. 1). Two unique bands (arrows) were detected in the samples containing mixtures of human brain cDNA and pCMVSPORTCAT cDNA (FIG. 1, lanes 2–5), which were not found in samples containing only brain cDNA alone (FIG. 1, lane 6). These bands co-migrated in the gel with two prominent bands found in a control sample containing only plasmid DNA (FIG. 1, lane 1). One of these unique bands was excised from the gel, amplified, and cloned into E. coli host cells via a pAMP-1 vector. Plasmid DNA isolated from transfected colonies was then run on a sequencing gel, and the nucleotide sequence of the unique fragment compared to known sequences in the GenBank sequence database. The cloned and amplified sequence was found to be homologous to the GenBank sequences of the chloramphenicol resistance gene. These results illustrate the ability of the AFLP-based method of the present invention to identify a library-specific DNA sequence.

Example 2

Figure 2:
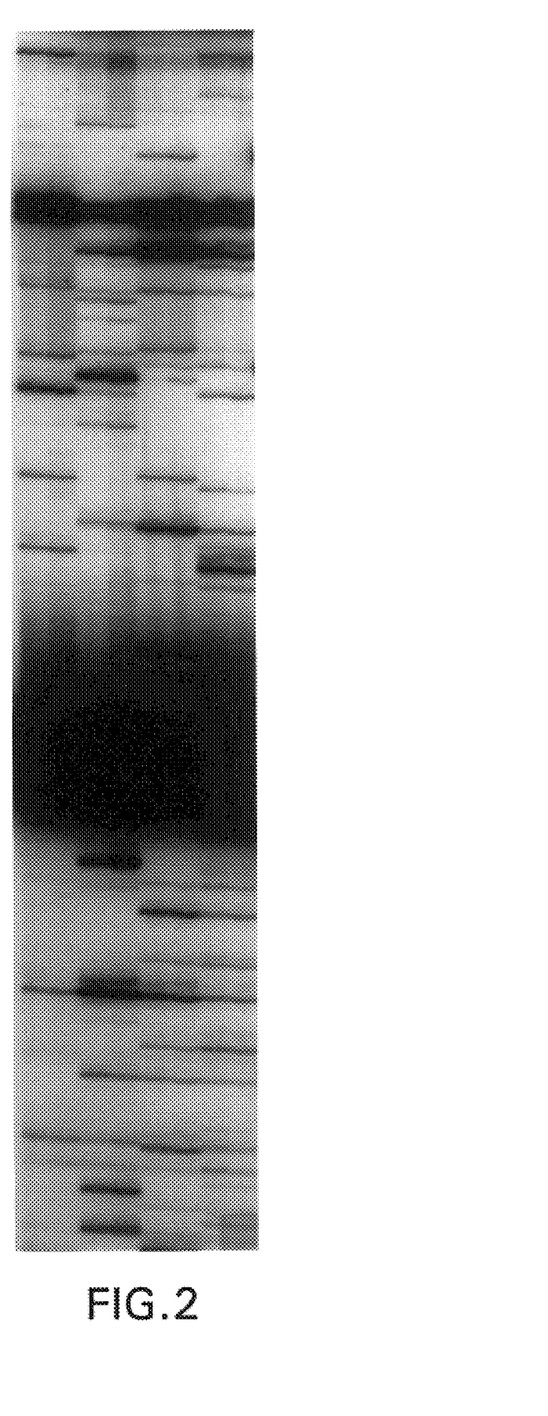
FIG. 2 is an autoradiogram of $^{32}$P-labeled EcoRI/MseI restriction fragments, separated by gel electrophoresis (5% polyacrylamide+8M urea sequencing gel), of samples prepared from cDNA libraries of human liver, leukocytes, kidney or brain (500 nanograms per sample). Lanes 1, 2: liver; Lanes 3, 4: leukocytes; Lanes 5, 6: kidney; Lanes 7, 8: brain. Arrow indicates a unique DNA fragment detected in brain cDNA.

To further demonstrate the utility of the AFLP-based method of the present invention to identify tissue-specific DNA sequences, AFLP was performed as described above on samples of cDNAs isolated from human brain, kidney, leukocyte and liver libraries (obtained from GEBCO/BRL, Gaithersburg, Md.), and the restriction patterns of these samples determined by gel electrophoresis (FIG. 2). At least one unique band (arrow) was detected in the samples from the brain cDNA library (FIG. 2, lanes 7, 8), which was not found in the samples prepared from the other tissue types (FIG. 2, lanes 1–6). This brain-specific fragment was excised from the gel, amplified and cloned into E. coli host cells using the pAMP-1 vector. Plasmid DNA purified from transfected colonies was sequenced via gel electrophoresis, and the sequence of the brain-specific fragment compared to known sequences in the GenBank sequence database. The cloned and amplified brain-specific fragment was found to be homologous to a brain-specific cDNA previously reported (Adams et al., Nature 355:632–634 (1992)). These results further illustrate the power of the AFLP-based method of the present invention in identifying a unique DNA sequence that is not found in other tissues.

Example 3

To demonstrate the utility of the AFLP-based method of the present invention in isolating and identifying DNA from a whole tissue, oligonucleotide probes were prepared from 20 brain-specific sequences resolved as in Example 2. These oligonucleotides were then used to obtain a full-length brain cDNA from a whole brain library by hybridization using GENETRAPPER (LTI). Using this approach, several cDNA clones were obtained, and one of these clones was sequenced by gel electrophoresis. Upon comparison with GenBank sequences, the isolated brain-specific cDNA was found to be identical to that reported previously from brain (Adams et al., Nature 355:632–634 (1992)). These results indicate that, in addition to its usefulness in identifying a DNA unique to a particular tissue type, the AFLP-based method of the present invention may be used for the isolation of a tissue-specific DNA fragment from a complex genome, tissue or cDNA library.

Example 4

To determine the efficacy of the present invention in distinguishing diseased plant tissues from those that are not diseased, mRNA was isolated from soybean (Glycine max L. Merr.) roots that were infected or not with cyst nematode. cDNA libraries were constructed from these mRNAs, and total cDNA was prepared from these two libraries and analyzed according to the present invention. Several unique DNA bands, identified in the cyst nematode-infected cDNA library but not in that from non-infected plants, were isolated from the sequencing gel. These unique fragments were amplified to EcoRI and MseI primers, annealed to pAMP-1, and transformed into E. coli as described above. After expansion of the cultures, plasmid DNAs containing the desired inserts were purified, blotted onto nylon membrane and hybridized to $^{32}$P-labeled cDNA prepared from the total RNA of either cyst nematode-infected or -noninfected plants. Two plasmid DNAs showed strong hybridization signals with the cDNA probe prepared from infected plants but not with those from noninfected plants. Upon sequencing and GenBank comparison, these two clones showed significant homology to pea (Pisum sativum). These results demonstrate that disease-inducible genes are capable of being identified by the AFLP-based methods of the present invention.

Example 5

To demonstrate the utility of the present invention in examining genetic relationships between different organisms, studies were conducted in a variety of microorganisms such as E. coli, Agrobacterium spp, Xanthomonas, Pseudomonas, and Collectotrichum. Genomic DNA was prepared from these organisms, digested with restriction enzymes and analyzed as above. Representations of the phenogenetic relationships between these organisms (such as dendrograms) were prepared by densitometric scanning of the resultant autoradiogram and analyzing the similarity (i.e., calculating a "percent similarity index") using computer programs for DNA fingerprinting analysis such as that available from Bio-Rad (Hercules, Calif.). The results of these studies demonstrate that DNA markers identified by the present invention provide a powerful means for the determination of familial genetic relationships between a variety of prokaryotic (and, by extension, eukaryotic) organisms. This technique should also prove useful for a determination of the distribution of infectious diseases throughout the world. Moreover, similar results can be achieved by applying this technique to cDNA libraries prepared from prokaryotic organisms.

Example 6

To demonstrate the utility of the present invention in identifying genetic markers, samples of genomic DNA from matched pairs of twins, wherein one individual was normal (unaffected) and the other was diagnosed as schizophrenic or bipolar, were analyzed by AFLP. As demonstrated in FIG. 3, a number of potential genetic markers were identified between these four pairs of twins. More importantly, several such potential markers were detected between matched pairs of twins (arrows); these genetic markers were most evident in the matched pair depicted in lanes 3 and 4 of FIG. 3A.

Figure 3A:
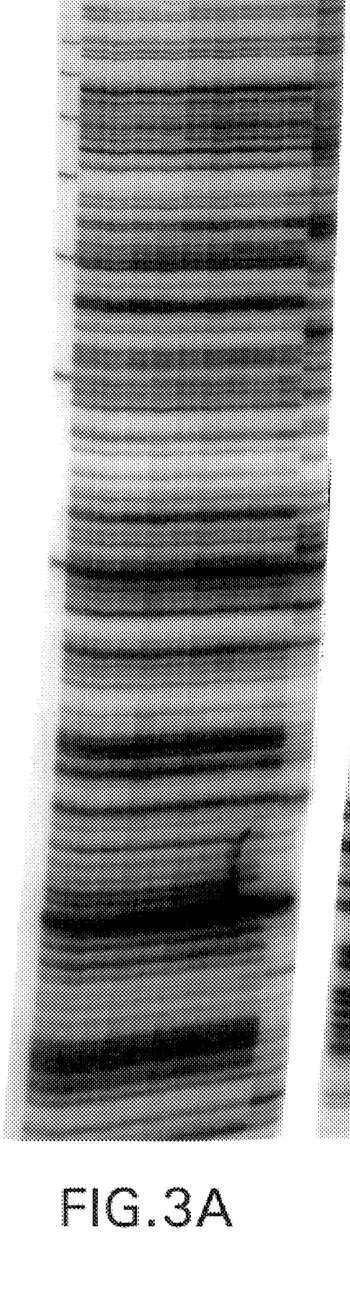
FIG. 3 is an autoradiogram of $^{32}$P-labeled EcoRI/MseI restriction fragments, separated by gel electrophoresis (5% polyacrylamide+8M urea sequencing gel), of samples from human genomic DNA from four pairs of identical twins (matched in lanes 1 and 2; lanes 3 and 4; lanes 5 and 6; lanes 7 and 8 of each panel), using the EcoRI primer shown in SEQ ID NO: 1, and either the MseI primer shown in SEQ ID NO:2 (panel A) or the MseI primer shown in SEQ ID NO:3 (panel B). Lane 1: unaffected; Lane 2: matched twin, schizophrenic. Lane 3: schizophrenic; lane 4: matched twin, unaffected. Lane 5: schizophrenic; lane 6: matched twin, unaffected. Lane 7: bipolar; lane 8: matched twin, unaffected. M: DNA sizing markers.
Figure 3B:
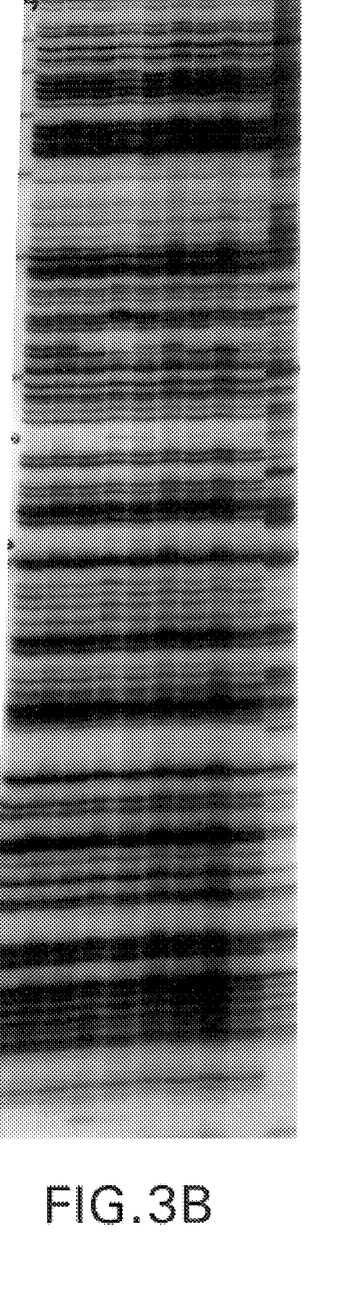

These unique DNA fragments between the individuals in lanes 3 and 4 were consistently detected even when alternative primer pairs were used for AFLP analysis (FIG. 3B; see lanes 3 and 4). These results indicate that the AFLP-based methods of the present invention provide a powerful way to identify genetic markers, based on subtle differences in genomic DNA, between individuals who may even be as closely related as identical twins.

Example 7

By the present invention, the genetic markers identified in Example 6 may be isolated and sequenced. Potential genetic markers such as those denoted by the arrows in FIG. 3 are excised from the sequencing gels, amplified using universal AFLP primers and cloned into pAMP-1 as described above. The DNA sequences of these amplified genetic markers are then determined, using any of various sequencing methodologies that are well-known in the art (Maxam, A. M. and Gilbert, W., Proc. Natl. Acad. Sci. USA 74:560–564 (1977); Sanger, F., et al, Proc. Natl. Acad Sci. USA 74:5463–5467 (1977)). Alternatively, sequencing of the genetic markers is accomplished using automated DNA sequencing apparatus. After sequencing, PCR primer sequences are constructed as described in U.S. Pat. Nos. 4,683,195; 4,683,202; and 4,800,159 and used for amplification of other samples of genomic DNA for AFLP determination of the presence of genetic markers for schizophrenia. In this way, the methods provided by the present invention allow the drawing of a physical diagnosis of schizophrenia to complement the accompanying psychological diagnosis. Moreover, isolated DNA sequences which have a functional open reading frame are used as target oligonucleotides for isolating and characterizing schizophrenia-related functional genes and the proteins encoded by such genes.

Example 8

Agrobactenium tumefaciens is a soil-dwelling plant pathogenic bacterium. The pathogenicity of certain strains of A. tumefaciens is imparted by the presence of the extrachromosomal Ti plasmid which is about 400 kilobases in size. Therefore, AFLP was performed on samples of genomic DNA from strains C58 (a pathogenic strain) and A136 (a nonpathogenic strain) of A. tumefaciens, to determine the presence of genetic markers distinguishing these strains.

Figure 4:
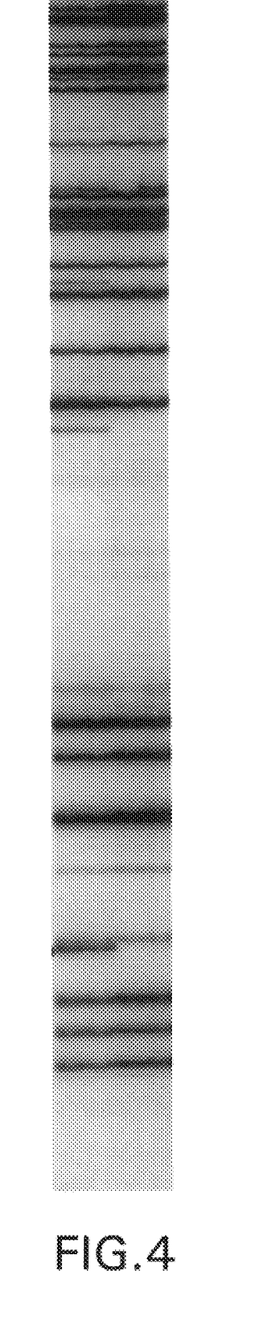
FIG. 4 is an autoradiogram of $^{32}$P-labeled EcoRI/MseI restriction fragments, separated by gel electrophoresis (5% polyacrylamide+8M urea sequencing gel), of samples prepared from genomic DNA of *Agrobacterium tumefaciens* strain C58 (lanes 1, 2) or strain A136 (lanes 3, 4).

As shown in FIG. 4, several potential genetic markers were observed in strain C58 (lanes 1 and 2; see arrows) that were not present in strain A136 (lanes 3 and 4). Six of these pathogen-specific markers were isolated from the gels, cloned into pAMP-1 vectors as described above, and characterized by DNA sequencing and Southern blot hybridization. Upon comparison of these unique genetic markers with available sequences in GenBank, four of the AFLP-defined genetic markers observed in A. tumefaciens strain C58 were found to correspond to functional genes in the Ti plasmid (see Table 1).

TABLE 1

Sequence Comparisons between clones containing AFLP-defined polymorphic DNA from A. *tumefaciens* strain C58 and genes from GenBank.

| A. *tumefaciens* strain | Number of clones with AFLP-defined genetic markers | Homologous genes from GenBank | Genomic Southern blot hybridization |
|---|---|---|---|
| C58 | 1 | acs gene within T-DNA of C58 nopaline plasmid | |
| C58 | 2 | pTiC58 virB, virG, and virC genes of C58 | |
| C58 | 3 | pinF1 and pinF2 genes from pTiA6 | |
| C58 | 4 | virE locus of pTiC58 | pTiC58, C58 genomic DNA |
| C58 | 5 | unidentified | pTiC58, C58 genomic DNA |
| C58 | 6 | unidentified | pTiC58, C58 genomic DNA |
| A6 | 1 | occR gene from pTiA6 | |
| A6 | 2 | ocotopine synthetase in T-DNA region of pTiAch5 | |

Figure 5:
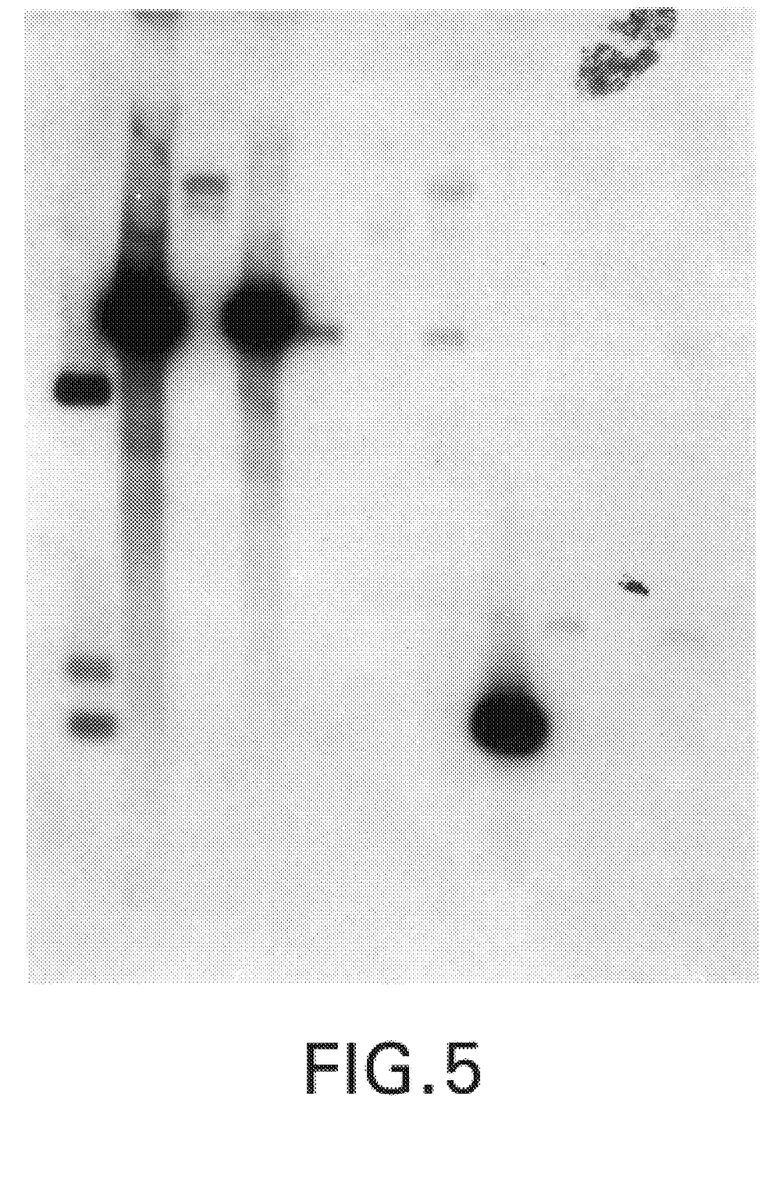
FIG. 5 is an autoradiogram of a Southern blot, using $^{32}$P-labeled C58 hybridization probes, of EcoRI (lanes 2–7) or EcoRI/MseI (lanes 8–11) restriction fragments of plasmid or genomic DNA from various strains of *A. tumefaciens*. Lane 1: 1 kilobase marker; lane 2: pTi58 sample; lane 3: pTiA6 sample; lanes 4 and 8: C58 genomic DNA samples; lanes 5 and 9: A136 genomic DNA samples; lanes 6 and 10: LBA4404 (strain Ach5) genomic DNA samples; lanes 7 and 11: A6 genomic DNA samples.

To determine their possible identity, the two unknown AFLP-defined genetic markers in strain C58 were further analyzed by examining their abilities to hybridize on Southern blots with plasmid or genomic DNA sequences from various strains of A. *tumefaciens*. As shown in FIG. 5, the two unknown AFLP-defined markers hybridized with Ti plasmid (lane 2) and genomic (lanes 4, 8) DNA sequences isolated from C58, but not with genomic DNA isolated from A. *tumefaciens* strain A136 (lanes 5, 9) or with genomic DNA or Ti plasmid sequences isolated from A. *tumefaciens* octopine-like strains Ach5 (lanes 6, 10) and A6 (lanes 3, 7, 11). Together, these results indicated that AFLP is capable of determining the presence of potential genetic markers of pathogenicity or virulence in different strains of bacteria.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for identifying a DNA fragment from a first cDNA library, said DNA fragment not being present in a second cDNA library, said method comprising the steps of:
   (a) digesting a first and second cDNA libraries with at least one restriction enzyme to give a collection of restriction fragments; and
   (b) identifying one or more unique fragments from said first cDNA library by comparing the fragments from said first library to fragments from said second library, with the proviso that the fragments are not subjected to subtractive hybridization before comparing.

2. The method of claim 1, wherein said identifying step is accomplished by separating the restriction fragments according to size.

3. The method of claim 1, wherein said restriction fragments are amplified prior to said identifying step (b).

4. The method of claim 1, wherein said restriction fragments are detectably labeled.

5. The method of claim 2, wherein said restriction fragments are amplified prior to said separation according to size.

6. The method of claim 1, further comprising the steps of:
   (c) isolating at least one unique DNA fragment; and
   (d) inserting s aid DNA fragment into a vector.

7. The method of claim 6, wherein said fragment is amplified prior to insertion into said vector.

8. The method of claim 1, further comprising sequencing said unique fragment.

9. A method for isolating a DNA molecule from a first cDNA library, said method comprising the steps of:
   (a) mixing one or more the unique fragments identified according to claim 1, or one or more oligonucleotide probes which are complementary to said fragments, with a first cDNA library under conditions stringent for hybridization of said unique fragments or oligonucleotide probes to said first cDNA library; and
   (b) isolating a DNA molecule which is complementary to said unique fragments or to said oligonucleotide probes.

10. The method of claim 9, wherein said isolation step is accomplished by a method selected from the group of methods consisting of gel electrophoresis, density gradient centrifugation, sizing chromatography, affinity chromatography, immunoadsorption, and immunoaffinity chromatography.

11. The method of claim 9, further comprising sequencing said isolated DNA molecule.

12. The method of claim 9, further comprising amplifying said isolated DNA molecule.

13. The method of claim 9, further comprising inserting said isolated DNA molecule into a vector.

14. The method of claim 13, wherein said vector is an expression vector.

15. The method of claim 3, wherein said amplification of said restriction fragments is accomplished by a method comprising:

(a) ligating one or more adapter oligonucleotides to said unique restriction fragments to form a DNA-adapter complex;

(b) hybridizing said DNA-adapter complex, under stringent conditions, with one or more oligonucleotide primers which are complementary to said adapter portion of said DNA-adapter complex to form a hybridization complex; and (c) amplifying said DNA-adapter complex.

16. The method of claim 15, wherein said adapter oligonucleotide contains one or more restriction sites.

17. The method of claim 16, wherein said restriction sites in said adapter are used to insert the DNA-adapter complex into a vector.

18. The method of claim 1, wherein said first cDNA library and said second cDNA library are derived from a source selected from the group consisting of an individual cell, a tissue, an organ, and a whole organism.

19. The method of claim 18, wherein said source is a prokaryotic cell.

20. The method of claim 18, wherein said source is a eukaryotic cell.

21. The method of claim 18, wherein said source is an animal tissue.

22. The method of claim 18, wherein said source is a human tissue.

23. The method of claim 18, wherein said source is a human embryo.

24. The method of claim 18, wherein said source is a human fetus.

25. The method of claim 18, wherein said source is a plant tissue.

26. A method for identifying a genetic marker in a first cDNA library, said method comprising the steps of:

(a) digesting first and second cDNA libraries with at least one restriction enzyme to give a collection of restriction fragments; and (b) identifying one or more unique DNA fragments from said first cDNA library by comparing the fragments from said first library to fragments from said second library, with the proviso that the fragments are not subjected to subtractive hybridization before comparing.

27. The method of claim 26, further comprising sequencing said unique DNA fragment.

28. The method of claim 26, wherein said restriction fragments are amplified prior to said identifying step (b).

29. The method of claim 27, wherein said genetic marker is selected from the group consisting of a cancer marker, an infectious disease marker, a genetic disease marker, a marker of embryonic development, a tissue-specific marker and an enzyme marker.

30. The method of claim 1 or claim 26, wherein said first cDNA library is derived from a sample of an animal suffering from cancer and said second cDNA library is derived from a animal not suffering from cancer.

31. The method of claim 1 or claim 26, wherein said first cDNA library is derived from a cancerous animal tissue and said second cDNA library is derived from a noncancerous animal tissue.

32. The method of claim 31, wherein said first library and said second library are derived from the same animal.

33. The method of claim 1 or claim 26, wherein said first cDNA library is derived from an animal suffering from a genetic disease and said second cDNA library is derived from an animal not suffering from said genetic disease.

34. The method of claim 33, wherein said genetic disease is schizophrenia.

35. The method of claim 1 or claim 26, wherein said first CDNA library is derived from a diseased plant and said second CDNA library is derived from a non-diseased plant.

36. The method of claim 1 or claim 26, wherein said first cDNA library is derived from a plant resistant to an environmental stress and said second CDNA library is derived from a plant not resistant to said environmental stress.

37. The method of claim 34, wherein said environmental stress is selected from the group consisting of drought, excess temperature, diminished temperature, chemical toxicity by herbicides, pollution, excess light and diminished light.

38. The method of claim 1 or claim 26, wherein said first cDNA library is derived from a pathogenic microorganism and said second cDNA library is derived from a nonpathogenic microorganism.

39. The method of claim 1 or claim 26, wherein said first cDNA library is derived from a organism producing an enzyme and said second cDNA library is derived from an organism not producing said enzyme.

40. The method of claim 39, wherein said enzyme is a restriction enzyme, an enzyme degrading a petroleum product, a biodegradative enzyme, a nucleic acid polymerase enzyme, a nucleic acid ligase enzyme, an amino acid synthetase enzyme or an enzyme involved in carbohydrate fermentation.

41. A method of determining the relationship between a first individual and a second individual, said method comprising the steps of:

(a) digesting cDNA libraries obtained from said first and second individuals with at least one restriction enzyme to give a collection of restriction fragments;

(b) separating said restriction fragments from said first and said second individual according to size; and (c) determining the similarities and dissimilarities of the sizes or concentrations of the restriction fragments separated in step (b), with the proviso that the fragments are not subjected to subtractive hybridization before determining the similarities or dissimilarities.

42. The method of claim 1 or claim 26, wherein said first cDNA library is derived from a source that is different from the source from which said second cDNA library is derived.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear    (ii) MOLECULE TYPE: cDNA    (xi) SEQUENCE DESCRIPTION: SEQ ID NO: 1:

CAUCAUCAUC AUGACTGCGT ACCAATTC          28

(2) INFORMATION FOR SEQ ID NO: 2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear    (ii) MOLECULE TYPE: cDNA    (xi) SEQUENCE DESCRIPTION: SEQ ID NO: 2:

GACTGCGTAC CAATTCACC          19

(2) INFORMATION FOR SEQ ID NO: 3:

```
        (i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 3:

CUACUACUAC UAGATGAGTC CTGAGTAA                                                    28

(2) INFORMATION FOR SEQ ID NO: 4:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 4:

GATGAGTCCT GAGTAACAA                                                              19

(2) INFORMATION FOR SEQ ID NO: 5:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 5:

GATGAGTCCT GAGTAACAC                                                              19
```